(12) United States Patent
Whitman et al.

(10) Patent No.: US 7,815,092 B2
(45) Date of Patent: Oct. 19, 2010

(54) STAPLE POCKET ARRANGEMENT FOR SURGICAL STAPLER

(75) Inventors: Michael P. Whitman, New Hope, PA (US); John E. Burbank, Ridgefield, CT (US)

(73) Assignee: Power Medical Interventions, LLC, Mansfield, MA (US)

( * ) Notice: Subject to any disclaimer, the term of this patent is extended or adjusted under 35 U.S.C. 154(b) by 0 days.

(21) Appl. No.: 11/495,011

(22) Filed: Jul. 27, 2006

(65) Prior Publication Data
US 2007/0057014 A1  Mar. 15, 2007

Related U.S. Application Data

(60) Provisional application No. 60/703,262, filed on Jul. 27, 2005.

(51) Int. Cl.
*A61B 17/068* (2006.01)
(52) U.S. Cl. .............. 227/181.1; 227/176.1; 227/178.1
(58) Field of Classification Search ................ 227/19, 227/175.1, 176.1, 181.1
See application file for complete search history.

(56) References Cited

U.S. PATENT DOCUMENTS

| | | | |
|---|---|---|---|
| 3,494,533 A | | 2/1970 | Green et al. |
| 5,480,089 A | * | 1/1996 | Blewett ................... 227/175.1 |
| 5,630,541 A | * | 5/1997 | Williamson et al. ...... 227/178.1 |
| 5,662,258 A | * | 9/1997 | Knodel et al. ............. 227/175.1 |
| 6,953,138 B1 | * | 10/2005 | Dworak et al. ........... 227/175.1 |
| 7,121,446 B2 | * | 10/2006 | Arad et al. ............... 227/176.1 |
| 2004/0267310 A1 | * | 12/2004 | Racenet et al. ............... 606/219 |

FOREIGN PATENT DOCUMENTS

EP          0 251 444 A        1/1988

OTHER PUBLICATIONS

Supplementary European Search Report—Application No. EP 06 78 8913. Date of Completion: Nov. 2, 1009; 6 pages.

\* cited by examiner

*Primary Examiner*—Rinaldi I. Rada
*Assistant Examiner*—Nathaniel Chukwurah
(74) *Attorney, Agent, or Firm*—Carter, DeLuca, Farrell & Schmidt, LLP

(57) ABSTRACT

A staple pocket arrangement on the anvil portion of a surgical stapler device includes pairs of staple pockets corresponding to each one of a plurality of staples to be closed. The staple pockets may have a generally triangular shape when viewed from above. Each respective staple leg is received at a longitudinal end of the staple pocket that provides a relatively wide target area for receiving the staple leg to eliminate or at least minimize the likelihood that a staple leg will miss the staple pocket due to, e.g., misalignment between a first jaw of the surgical stapler having the anvil and a second jaw of the surgical stapler having a cartridge configured to fire the staples. The staple pockets may be arranged in rows, each row of staple pockets being longitudinally offset from another row, such that each staple pocket in a first row of staple pockets is nested with a staple pocket from an adjacent row of staple pockets to make more efficient use of space on the anvil.

42 Claims, 7 Drawing Sheets

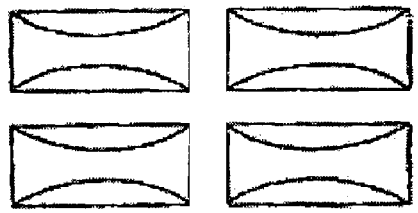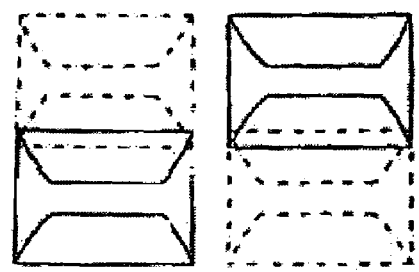
Figure 1
(PRIOR ART)

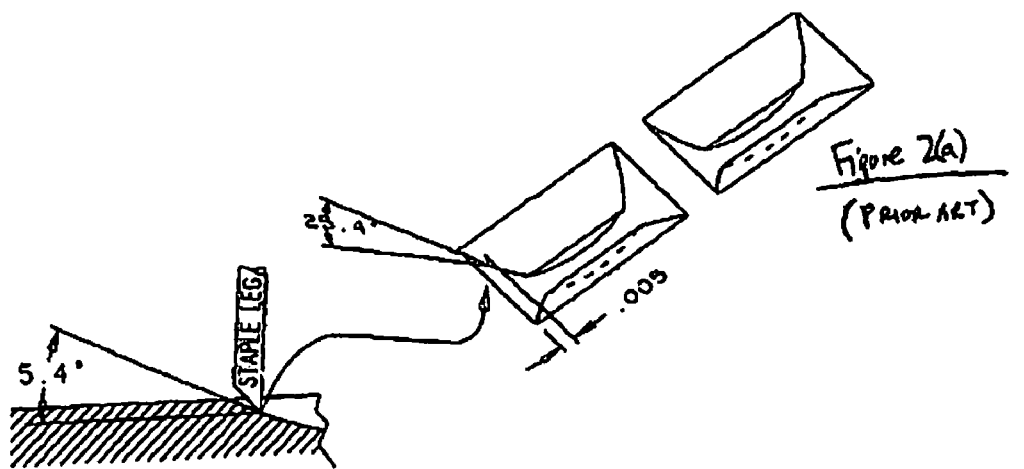
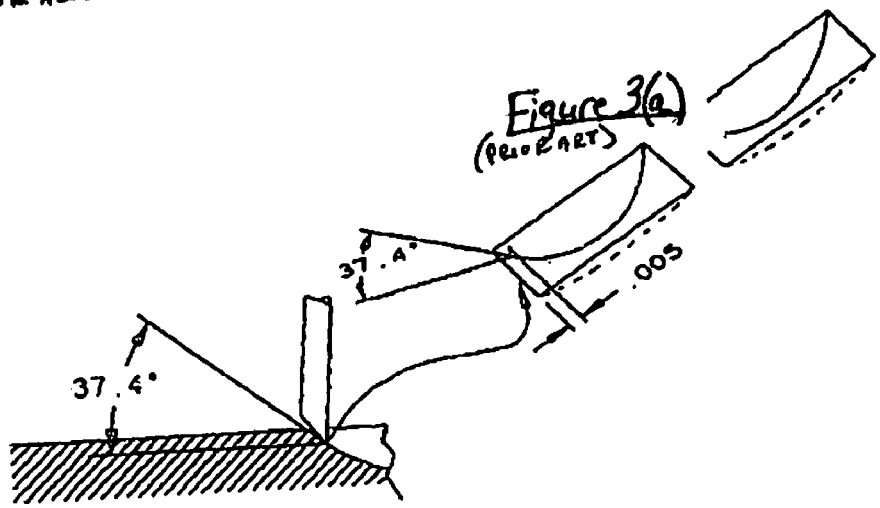

STAPLE POCKET ARRANGEMENT FOR SURGICAL STAPLER

CROSS-REFERENCE TO RELATED APPLICATIONS

This application claims the benefit of U.S. Provisional Patent Application Ser. No. 60/703,262, entitled "Staple Pocket Arrangement for Surgical Stapler", filed Jul. 27, 2005, which is expressly incorporated herein in its entirety by reference thereto.

FIELD OF THE INVENTION

The present invention relates to a staple pocket. More specifically, the present invention relates to a staple pocket arrangement for use in a surgical stapler.

BACKGROUND INFORMATION

Surgical staplers typically employ an anvil having staple pockets defined therein. Staples are pushed out of a staple cartridge through a section of tissue and against the staple pockets, the staple pockets being shaped so as to receive and progressively bend the legs of the staple into a closed position. FIG. 1 is a top view of a portion of conventional staple pocket arrangements on the anvil of a surgical stapler, e.g., a first arrangement on the upper side of the knife slot and a second arrangement on the lower side of the knife slot. Conventional staple pockets are typically rectangular in shape and maybe arranged in parallel rows.

FIG. 2(a) is a bottom perspective view of a conventional staple pocket arrangement on the anvil of a surgical stapler. This staple pocket arrangement employs a steep canyon wall near the floor of the canyon which changes to a shallow angle for the rest of the canyon wall. FIG. 2(b) is a cross-sectional view of a portion of the staple pocket illustrated in FIG. 2(a). FIG. 2(b) illustrates the staple leg being received within the staple pocket, e.g., moving in a vertical direction, and prior to the staple leg being bent into a closed position. The angle of 25.4 degrees shown in FIGS. 2(a) and 2(b) is the angle of the surface of the staple pocket relative to the plane of the anvil surface, e.g., the slope angle of the surface along which the staple leg slides when the staple leg is initially received within the staple pocket at a location about 0.005 inches from the longitudinal edge of the staple pocket.

FIG. 3(a) is a bottom perspective view of another conventional staple pocket arrangement on the anvil of a surgical stapler. This staple pocket arrangement employs a steep canyon wall near the floor of the canyon which changes to a shallow angle for the rest of the canyon wall. FIG. 3(b) is a cross-sectional view of a portion of the staple pocket illustrated in FIG. 3(a). FIG. 3(b) illustrates the staple leg being received within the staple pocket, e.g., moving in a vertical direction, and prior to the staple leg being bent into a closed position. The angle of 37.4 degrees shown in FIGS. 3(a) and 3(b) is the angle of the surface of the staple pocket relative to the plane of the anvil surface, e.g., the slope angle of the surface along which the staple leg slides when the staple leg is initially received within the staple pocket at a location about 0.005 inches from the longitudinal edge of the staple pocket.

FIG. 4 is a top view of a portion of another conventional staple pocket arrangement on the anvil of a surgical stapler. In this arrangement, there are three longitudinal rows of the staple pockets located on each side of the knife slot.

One problem that may be encountered by conventional surgical staple pocket arrangements is that the staple pockets have sharp internal corners that may contribute to snagging or stalling the staple leg of a staple as the staple leg is progressively moved through the staple pocket. Another problem that may be encountered by conventional surgical staple pocket arrangements is that the staple pockets have a narrow capture area, such that staples that are slightly mis-aligned relative to the staple pockets may miss the pocket. Another problem that may be encountered by conventional surgical staple pocket arrangements is that the staple pockets may have too shallow a slope spread over a broad area so that incoming staple legs do not encounter a sufficiently steep slide angle, thereby causing the staple legs to stall and buckle.

SUMMARY

According to an example embodiment of the present invention, a staple pocket arrangement on the anvil portion of a surgical stapler device includes pairs of staple pockets corresponding to each one of a plurality of staples to be closed. The pair of staple pockets may be arranged along a center line. A distal staple pocket may be provided for receiving and closing a distal-most leg of a staple, and a proximal staple pocket may be provided for receiving and closing a proximal-most leg of a staple. The distal staple pocket may be a mirror image of the proximal staple pocket.

The staple pockets may have a generally triangular shape when viewed from above. Each respective staple leg is received at a longitudinal end of the staple pocket that provides a relatively wide target area for receiving the staple leg to eliminate or at least minimize the likelihood that a staple leg will miss the staple pocket due to, e.g., misalignment between a first jaw of the surgical stapler having the anvil and a second jaw of the surgical stapler having a cartridge configured to fire the staples. Furthermore, each of the staple pockets is narrower at its opposite end, e.g., the end at which the staple leg emerges after being formed into an arc by the curved canyon floor of the staple pocket. The staple pocket 110 may provide canyon walls, e.g., along which a staple leg is guided, that are steeply angled for the entire wall so that the staple leg travels toward and along the center of the canyon and then up and out the narrow end of the canyon. The floor of the canyon may have a generally smooth and continuous curvature which provides, during bending of the staple leg, sufficiently large radii of curvature so as to eliminate or at least minimize tight corners that may snag or impede staple legs that are moving along the surface.

Each staple pocket in a first row of staple pockets may be nested with a staple pocket from an adjacent row of staple pockets. In this manner, when each row of staple pockets is longitudinally offset from another row, e.g., by approximately one half of the pocket-pair (or staple) center-to-center pitch, the proximal staple pocket of a first row nests with a distal staple pocket of a second row. The staple pocket arrangement may be more tolerant of poorly aimed staples, may make more efficient use of space on the anvil and may be less likely to cause a staple jam or buckling of the staple leg.

BRIEF DESCRIPTION OF THE DRAWINGS

FIG. 1 is a top view of a portion of a conventional staple pocket arrangement on the anvil of a surgical stapler;

FIG. 2(a) is a bottom perspective view of a conventional staple pocket arrangement on the anvil of a surgical stapler;

FIG. 2(b) is a cross-sectional view of a portion of the staple pocket illustrated in FIG. 2(a);

FIG. 3(a) is a bottom perspective view of another conventional staple pocket arrangement on the anvil of a surgical stapler;

FIG. 3(b) is a cross-sectional view of a portion of the staple pocket illustrated in FIG. 3(a);

DETAILED DESCRIPTION

Figure 4:
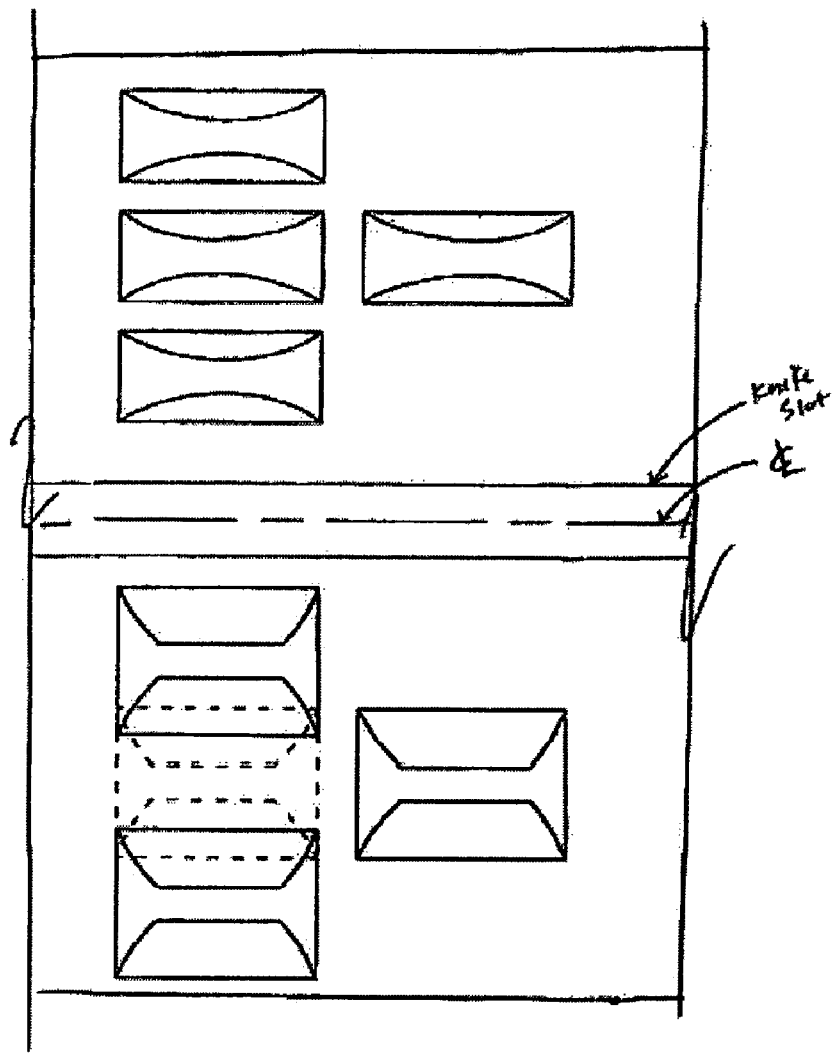
FIG. 4 is a top view of a portion of another conventional staple pocket arrangement on the anvil of a surgical stapler.
Figure 5:
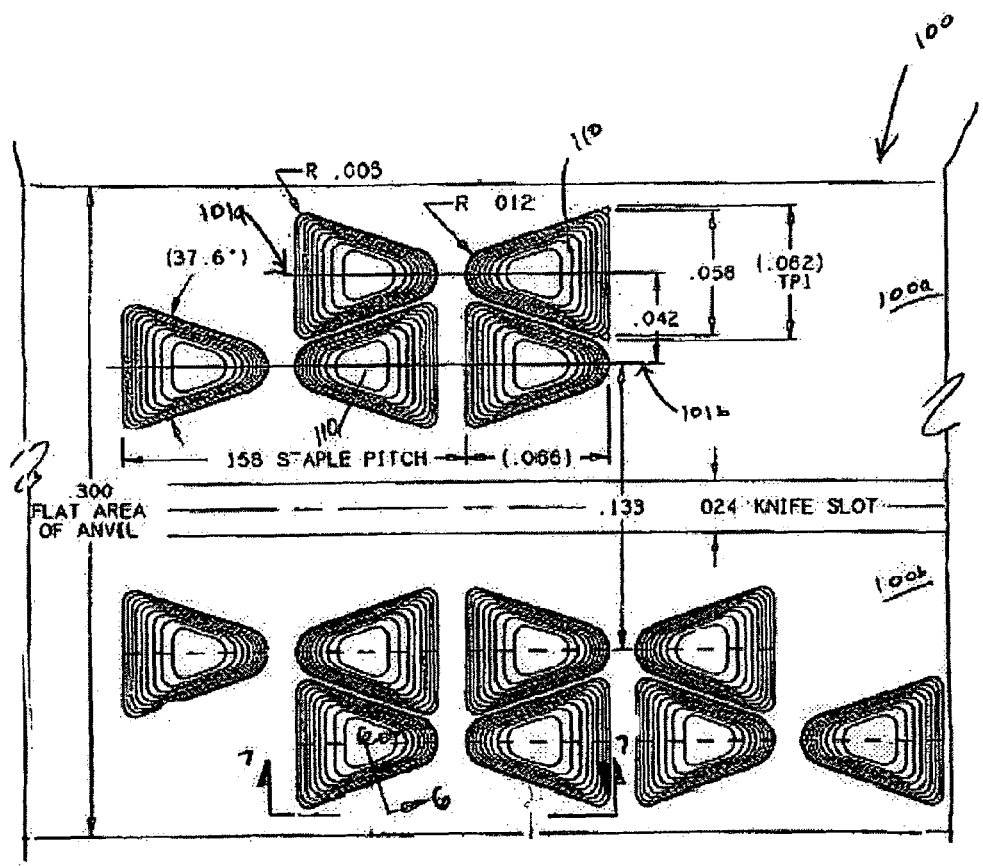
FIG. 5 is a top view of a staple pocket arrangement on the anvil of a surgical stapler, in accordance with an example embodiment of the present invention.

FIG. 5 is a top view of a staple pocket arrangement on the anvil of a surgical stapler, in accordance with an example embodiment of the present invention. Specifically, FIG. 5 illustrates an anvil surface 100 having a first side 100a and a second side 100b separated by a knife slot. On each of the first side 100a and the second side 100b of the anvil surface 100 there is defined two rows of staple pockets 110. Referring to the first side 100a of the anvil surface 100, a first row of staple pockets 110 has a center line 101a and a second row of staple pockets 110 has a center line 101b. For the purposes of clarity, only several staple pockets 110 have been shown. However, the anvil surface 100 may have any number of staple pockets 100 in each of the rows. Furthermore, while exemplary embodiments described herein include rows of staple pockets that are arranged adjacent to a knife slot, exemplary embodiments of the present invention maybe employed in connection with any type of surgical stapler, e.g., with or without a knife slot or any other structural feature.

The anvil surface 100 is arranged with pairs of staple pockets 110 corresponding to each staple to be closed. For instance, referring to the pair of staple pockets 110 arranged along the center line 101a, there is provided a distal staple pocket for receiving and closing a distal-most leg of a staple, and a proximal staple pocket for receiving and closing a proximal-most leg of a staple. The distal staple pocket 110 may be a mirror image of the proximal staple pocket 110.

The staple pockets 110 may have various shapes. As shown in FIG. 5, each staple pocket 110 may be roughly triangular in shape when viewed from above. Alternatively, each staple pocket 110 may have a shape when viewed from above that resembles a "bicycle seat", e.g., being generally triangular and having a series of convex and concave curves along its sides. Other shapes may also be employed.

Each respective staple leg is received at a longitudinal end of the staple pocket 110 that provides a relatively wide target area for receiving the staple leg. Since the staple pocket 110 is relatively wide at the longitudinal end at which the staple leg is received, the staple pocket arrangement may eliminate or at least minimize the likelihood that a staple leg will miss the staple pocket due to, e.g., misalignment between a first jaw of the surgical stapler having the anvil and a second jaw of the surgical stapler having a cartridge configured to fire the staples.

Figure 7:
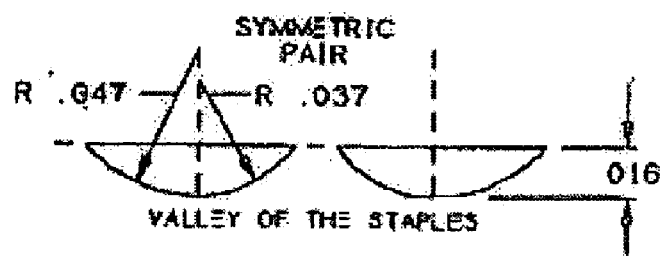
FIG. 7 is a cross-sectional view, taken along lines 7-7, of a portion of the staple pocket illustrated in FIG. 5.
Figure 6:
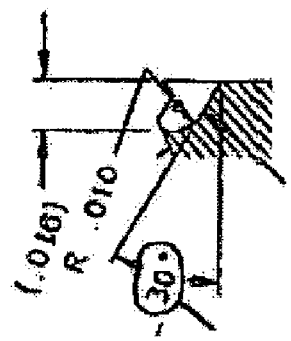
FIG. 6 is a cross-sectional view, taken along lines 6-6, of a portion of the staple pocket illustrated in FIG. 5.

Each of the staple pockets 110 is narrower at its opposite end, e.g., the end at which the staple leg emerges after being formed into an arc by the curved canyon of the staple pocket 110. The staple pocket 110 provides staple guidance in that the canyon walls along which a staple leg is guided are steeply angled for the entire wall (see, for instance, FIG. 6) so that the staple leg travels toward and along the center of the canyon and then up and out the far end narrow end of the canyon. The floor of the canyon has a generally smooth and continuous curvature which provides for the bending of the staple leg, as shown, for example, in FIG. 7. Alternatively or additionally, the floor of the canyon may have changing radii. The surfaces of the staple pockets are joined to each other with sufficiently large radii so as to eliminate or at least minimize tight corners that may snag or impede staple legs that are moving along the surface. Furthermore, the compound angle between these surfaces provides a sufficiently steep slide ramp for the staple legs to follow. The staples follow these slide ramps down into the canyon for proper bending or forming even when the staple is not well aimed by the cartridge.

Figure 8:
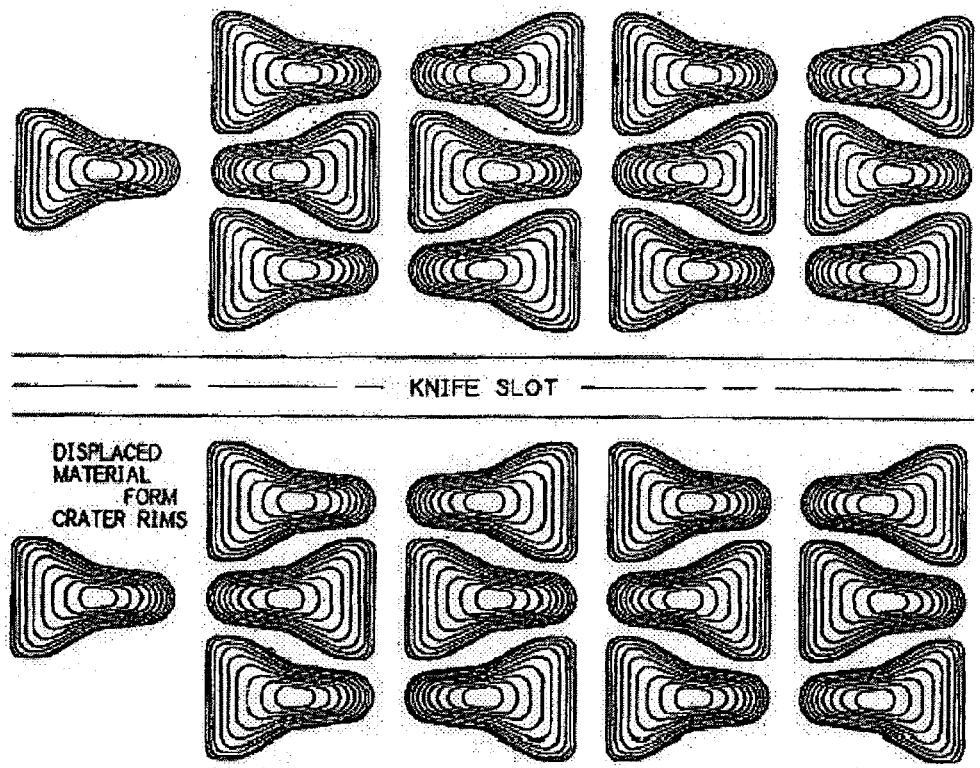
FIG. 8 is a top view of a staple pocket arrangement on the anvil of a surgical stapler, in accordance with an example embodiment of the present invention.
Figure 9:
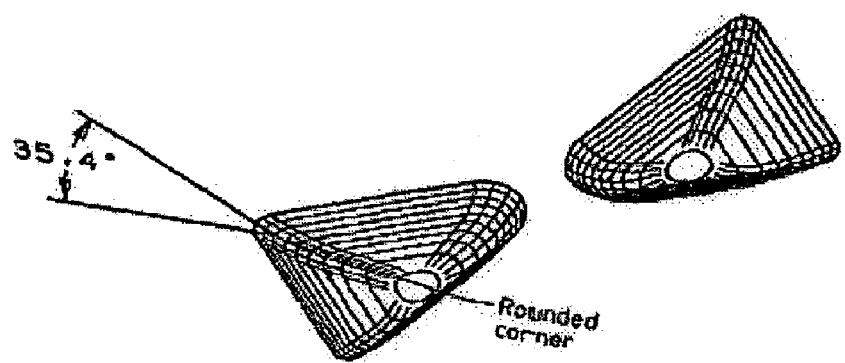
FIG. 9 is a bottom perspective view of another staple pocket arrangement on the anvil of a surgical stapler, in accordance with an example embodiment of the present invention.

Since this opposite end of the staple pocket 110 is relatively narrow, each staple pocket 110 in a first row of staple pockets 110 may be nested with a staple pocket from an adjacent row of staple pockets. Each row of staple pockets (and corresponding staples) may be longitudinally offset from another row, e.g., by approximately one half of the pocket-pair (or staple) center-to-center pitch. Thus, the proximal staple pocket of a first row nests with a distal staple pocket of a second row as shown in FIG. 5. In an example embodiment, see, for instance FIG. 8, a third row of staple pockets may be provided wherein the distal staple pocket of the second row also nests with the proximal staple pocket of the third row.

A series of staple pocket-pairs is formed in the anvil of a surgical stapling device. The number of staple pocket-pairs and their location depends upon the desired staple pattern desired. Typically, there will be several rows of pockets arranged alongside, e.g., parallel to, each other. For example, the sides of the staple pocket, e.g., those portions between the inner and outer longitudinal ends, may be angled relative to a center line of the row. In such an arrangement, when the staple pocket in the first row of staple pockets is nested with the staple pocket from the second row of staple pockets, adjacent sides of the staple pockets may be generally parallel to each other.

The section of tissue is clamped between the anvil and a cartridge loaded with staples. Each staple in the cartridge is generally aligned with a corresponding pair of staple pockets. Upon firing, the staples are pushed out of the cartridge so that the legs of the staples penetrate the section of tissue and proceed into the respective staple pockets. Continuous operation of the staple firing mechanism causes the staple legs to be received into the wide end of the staple pocket 110 and to slide along the curved valley of the pocket to bend or form in accordance with the curvature of the staple pocket. Eventually, the legs of each staple are fully bent or formed such that the section of tissue is held between the spine of the staple and the bent staple legs.

The surgical staple pocket arrangement may provide advantages over the staple pocket arrangements of conventional surgical stapler devices. For instance, the staple pocket arrangement hereof may provide an incoming staple leg capture area that is more tolerant of poorly aimed staples, e.g., that is able to receive and effectively bend a staple leg that is slightly mis-aligned relative to the center line of the staple pocket. This is due at least in part to the wide capture area located at the outer longitudinal end of the staple pockets and to the staple pockets' generally triangular shape. Thus, one feature of the staple pockets hereof is the provision of a wide capture area at one end of the staple pocket, which permits effective operation of the surgical stapler device even for staple legs arriving off-center due to a reasonable amount of misalignment between the anvil and the staple cartridge. Another feature hereof is that sharp corners which tend to snag the ends of staple legs are eliminated or at least minimized. Another feature hereof is that regardless of where the end of the staple leg arrives across the broad end of the pocket, there is a sufficiently steep slope or sliding angle so that the staple leg is induced to follow the forming curvature of the pocket. The steep sidewalls of the staple pocket function to guide the staple leg back towards the center of the staple as the staple leg gets bent or formed, regardless of off-center arrival of the staple leg. Rows of these pockets may be neatly nested alongside each other in close proximity, e.g., when phase shifted by approximately one half of the pocket-pair pitch. This nesting of the staple pockets of adjacent rows of staple pockets allows each staple pocket to have a greater staple capture area and permits adjacent rows of staple pockets to be spaced closer together.

In summary, the arrangement hereof may provide, relative to conventional staple pocket arrangements, a wider staple leg input capture area, a steeper slide angle to induce the staple to start forming, a shape that allows rows to be nested efficiently and an arrangement in which the radii of curvature of the staple pockets are broader than the radius of the staple wire. The staple pocket arrangement may eliminate or at least minimize sharp corners which may tend to snag staples. Thus, the staple pocket arrangement may be more tolerant of poorly aimed staples, makes more efficient use of space on the anvil and is less likely to cause a staple jam or buckling.

The staple pocket arrangement hereof may be formed by various manufacturing methods. For example, the staple pocket arrangement may be formed as described, e.g., in U.S. Provisional Patent Application No. 60/703,493, entitled "System and Method for Forming Staple Pockets of a Surgical Stapler", filed on Jul. 27, 2005, and in U.S. patent application Ser. No. _____, entitled "System and Method for Forming Staple Pockets of a Surgical Stapler," filed on Jul. 27, 2006, each of which is expressly incorporated herein in its entirety by reference thereto.

What is claimed is:

1. A surgical stapler device for closing staples, each staple having a distal staple leg and a proximal staple leg, the device comprising:

an anvil portion including at least two rows of staple pockets, each one of the at least two rows including a pair of staple pockets corresponding to each staple, each pair of staple pockets including a distal staple pocket for receiving and closing the distal staple leg of the corresponding staple and a proximal staple pocket for receiving and closing the proximal staple leg of the corresponding staple, wherein a staple pocket in a first row of staple pockets is nested with a staple pocket from a second row of staple pockets, wherein each side of each staple pocket of the pair of staple pockets has a series of convex and concave curves when viewed from above, and wherein a distance between a longitudinal centerline of the first row of staple pockets and a longitudinal centerline of the anvil portion is greater than a distance between a longitudinal centerline of the second row of staple pockets and the longitudinal centerline of the anvil portion, and wherein a distance between the longitudinal centerline of the first row of staple pockets and the longitudinal centerline of the second row of staple pockets is less than a maximum width of each staple pocket.

2. The surgical stapler device of claim 1, wherein a first of a distal and a proximal staple pocket of a first row is nested with a second of a distal and a proximal staple pocket of a second row.

3. The surgical stapler device of claim 2, wherein the staple pockets of the first row are longitudinally offset from the staple pockets of the second row.

4. The surgical stapler device of claim 3, wherein the staple pockets of the first row are longitudinally offset from the staple pockets of the second row by one half of a center-to-center pitch of a pair of staple pockets.

5. The surgical stapler device of claim 3, wherein each staple pocket of the pair of staple pockets has a generally triangular shape when viewed from above.

6. The surgical stapler device of claim 1, wherein, in each row of the at least two rows, the staple pockets are arranged along a center line.

7. The surgical stapler device of claim 6, wherein, in each pair of staple pockets, a first one of a distal and a proximal staple pocket is a mirror image of a second one of the distal and the proximal staple pocket.

8. The surgical stapler device of claim 1, wherein, for each one of the staple pockets, an outer longitudinal end of the staple pocket is wider than an inner longitudinal end of the staple pocket.

9. The surgical stapler device of claim 8, wherein the outer longitudinal end of each staple pocket is configured to first receive a respective staple leg.

10. The surgical stapler device of claim 9, wherein each one of the staple pockets includes a curved canyon floor which forms a respective staple leg into an arc as the staple leg is received and pushed into the curved canyon floor of the staple pocket.

11. The surgical stapler device of claim 10, wherein each staple pocket includes walls along which a staple leg is guided, the walls being steeply angled.

12. The surgical stapler device of claim 10, wherein the canyon floor has a generally smooth and continuous curvature.

13. The surgical stapler device of claim 12, wherein the floor of each staple pocket includes radii of curvature that at least minimize tight corners that may snag or impede staple legs that are moving along the surface during bending of a respective staple leg.

14. The surgical stapler device of claim 1, wherein a distance between a longitudinal centerline of the first row of staple pockets and a longitudinal centerline of the anvil portion is greater than a distance between a longitudinal centerline of the second row of staple pockets and the longitudinal centerline of the anvil portion, and wherein at least a portion of each staple pocket in the first row of staple pockets is closer to the longitudinal centerline of the anvil portion than is at least a portion of each correspondingly nested staple pocket in the second row of staple pockets.

15. The surgical stapler device of claim 1, wherein a distance between a longitudinal centerline of the first row of staple pockets and a longitudinal centerline of the anvil portion is greater than a distance between a longitudinal centerline of the second row of staple pockets and the longitudinal centerline of the anvil portion, and wherein a radially inner-most edge of a staple pocket in the first row of staple pockets is closer to the longitudinal centerline of the anvil portion than is a radially outer-most edge of a correspondingly nested staple pocket in the second row of staple pockets, the radially inner-most edge and the radially outer-most edge being defined radially relative to the longitudinal centerline of the anvil portion.

16. The surgical stapler device of claim 1, wherein adjacent sides of staple pockets in the first and second rows of staple pockets are angled relative to a longitudinal centerline of the anvil portion and are generally parallel to each other.

17. A surgical stapler device for closing at least one staple having a distal staple leg and a proximal staple leg, the device comprising:
an anvil portion including a pair of staple pockets corresponding to each staple, the pair of staple pockets including a distal staple pocket for receiving and closing the distal staple leg of the corresponding staple and a proximal staple pocket for receiving and closing the proximal staple leg of the corresponding staple, wherein each staple pocket of the pair of staple pockets has a generally triangular shape when viewed from above,
wherein each side of the generally triangular shape of each staple pocket of the pair of staple pockets has a series of convex and concave curves when viewed from above, and
wherein a staple pocket in a first row of staple pockets is nested with a staple pocket from a second row of staple pockets, wherein a distance between a longitudinal centerline of the first row of staple pockets and a longitudinal centerline of the anvil portion is greater than a distance between a longitudinal centerline of the second row of staple pockets and the longitudinal centerline of the anvil portion, and wherein a distance between the longitudinal centerline of the first row of staple pockets and the longitudinal centerline of the second row of staple pockets is less than a maximum width of each staple pocket.

18. The surgical stapler device of claim 17, wherein, in each one of the pair of staple pockets, a proximal staple pocket is a mirror image of a distal staple pocket.

19. The surgical stapler device of claim 17, wherein each one of the staple pockets includes a curved canyon floor which forms a respective staple leg into an arc as the staple leg is received and pushed into the curved canyon floor of the staple pocket.

20. The surgical stapler device of claim 19, wherein the canyon floor has a generally smooth and continuous curvature.

21. The surgical stapler device of claim 20, wherein the floor of each staple pocket includes radii of curvature that at least minimize tight corners that may snag or impede staple legs that are moving along the surface during bending of a respective staple leg.

22. The surgical stapler device of claim 17, wherein each staple pocket includes walls along which a staple leg is guided, the walls being steeply angled.

23. The surgical stapler device of claim 17, wherein the anvil portion includes at least two rows of staple pockets, each one of the at least two rows including at least a pair of staple pockets, wherein a staple pocket in a first row of staple pockets is nested with a staple pocket from a second row of staple pockets.

24. The surgical stapler device of claim 23, wherein a first of a distal and a proximal staple pocket of a first row is nested with a second of a distal and a proximal staple pocket of a second row.

25. The surgical stapler device of claim 24, wherein the staple pockets of the first row are longitudinally offset from the staple pockets of the second row.

26. The surgical stapler device of claim 25, wherein the staple pockets of the first row are longitudinally offset from the staple pockets of the second row by one half of a center-to-center pitch of a pair of staple pockets.

27. The surgical stapler device of claim 23, wherein, in each row of the at least two rows, the staple pockets are arranged along a center line.

28. The surgical stapler device of claim 23, wherein the sides of the staple pocket between the inner and outer longitudinal ends are angled relative to the center line.

29. The surgical stapler device of claim 28, wherein, when the staple pocket in the first row of staple pockets is nested with the staple pocket from the second row of staple pockets, adjacent sides of the staple pockets are generally parallel to each other.

30. The surgical stapler device of claim 17, wherein, for each one of the staple pockets, an outer longitudinal end of the staple pocket is wider than an inner longitudinal end of the staple pocket.

31. The surgical stapler device of claim 30, wherein the outer longitudinal end of each staple pocket is configured to first receive a respective staple leg.

32. The surgical stapler device of claim 17, wherein a staple pocket in a first row of staple pockets is nested with a staple pocket from a second row of staple pockets, wherein a distance between a longitudinal centerline of the first row of staple pockets and a longitudinal centerline of the anvil portion is greater than a distance between a longitudinal centerline of the second row of staple pockets and the longitudinal centerline of the anvil portion, and wherein at least a portion of each staple pocket in the first row of staple pockets is closer to the longitudinal centerline of the anvil portion than is at least a portion of each correspondingly nested staple pocket in the second row of staple pockets.

33. The surgical stapler device of claim 17, wherein a staple pocket in a first row of staple pockets is nested with a staple pocket from a second row of staple pockets, wherein a distance between a longitudinal centerline of the first row of staple pockets and a longitudinal centerline of the anvil portion is greater than a distance between a longitudinal centerline of the second row of staple pockets and the longitudinal centerline of the anvil portion, and wherein a radially innermost edge of a staple pocket in the first row of staple pockets is closer to the longitudinal centerline of the anvil portion than is a radially outer-most edge of a correspondingly nested staple pocket in the second row of staple pockets, the radially innermost edge and the radially outer-most edge being defined radially relative to the longitudinal centerline of the anvil portion.

34. An anvil comprising at least two rows of staple pockets, each one of the at least two rows including a pair of staple pockets, each pair of staple pockets corresponding to a single staple and including a distal staple pocket and a proximal staple pocket, wherein a staple pocket in a first row of staple pockets is nested with a staple pocket from a second row of staple pockets,
wherein each side of each staple pocket of the pair of staple pockets has a series of convex and concave curves when viewed from above, and
wherein a distance between a longitudinal centerline of the first row of staple pockets and a longitudinal centerline of the anvil portion is greater than a distance between a longitudinal centerline of the second row of staple pockets and the longitudinal centerline of the anvil portion, and wherein a distance between the longitudinal centerline of the first row of staple pockets and the longitudinal centerline of the second row of staple pockets is less than a maximum width of each staple pocket.

35. The anvil of claim 34, wherein the staple pockets of the first row are longitudinally offset from the staple pockets of the second row.

36. The anvil of claim 34, wherein each staple pocket of the pair of staple pockets has a generally triangular shape when viewed from above.

37. The anvil of claim 36, wherein, in each pair of staple pockets, a distal staple pocket is a mirror image of a proximal staple pocket.

38. The anvil of claim 34, wherein each one of the staple pockets includes a curved floor having a generally smooth and continuous curvature including radii of curvature that at least minimize tight corners.

39. The anvil of claim 38, wherein each staple pocket includes walls that are steeply angled.

40. The anvil of claim 34, wherein a distance between a longitudinal centerline of the first row of staple pockets and a longitudinal centerline of the anvil portion is greater than a distance between a longitudinal centerline of the second row of staple pockets and the longitudinal centerline of the anvil portion, and wherein at least a portion of each staple pocket in the first row of staple pockets is closer to the longitudinal centerline of the anvil portion than is at least a portion of each correspondingly nested staple pocket in the second row of staple pockets.

41. The anvil of claim 34, wherein a distance between a longitudinal centerline of the first row of staple pockets and a longitudinal centerline of the anvil portion is greater than a distance between a longitudinal centerline of the second row of staple pockets and the longitudinal centerline of the anvil portion, and wherein a radially inner-most edge of a staple pocket in the first row of staple pockets is closer to the longitudinal centerline of the anvil portion than is a radially outer-most edge of a correspondingly nested staple pocket in the second row of staple pockets, the radially inner-most edge and the radially outer-most edge being defined radially relative to the longitudinal centerline of the anvil portion.

42. The anvil of claim 34, wherein adjacent sides of staple pockets in the first and second rows of staple pockets are angled relative to a longitudinal centerline of the anvil portion and are generally parallel to each other.

* * * * *